(12) United States Patent
Zhu et al.

(10) Patent No.: US 12,082,857 B2
(45) Date of Patent: Sep. 10, 2024

(54) ORTHOPEDIC IMPLANTATION OPERATION SYSTEM

(71) Applicant: SHENZHEN FUTURTEC MEDICAL CO., LTD., Shenzhen (CN)

(72) Inventors: Shengxiao Zhu, Shenzhen (CN); Linzhi Shi, Shenzhen (CN); Jiarui Chen, Shenzhen (CN); Tao Zhang, Shenzhen (CN)

(73) Assignee: SHENZHEN FUTURTEC MEDICAL CO., LTD., Shenzhen (CN)

( * ) Notice: Subject to any disclaimer, the term of this patent is extended or adjusted under 35 U.S.C. 154(b) by 343 days.

(21) Appl. No.: 17/561,702

(22) Filed: Dec. 23, 2021

(65) Prior Publication Data

US 2023/0017771 A1 Jan. 19, 2023

(30) Foreign Application Priority Data

Jul. 16, 2021 (CN) .......................... 202121629860.3

(51) Int. Cl.
 *A61B 17/70* (2006.01)
 *A61B 17/16* (2006.01)
 (Continued)

(52) U.S. Cl.
 CPC ...... *A61B 17/7082* (2013.01); *A61B 17/1671* (2013.01); *A61B 34/20* (2016.02);
 (Continued)

(58) Field of Classification Search
 CPC .................................................. A61B 17/7082
 See application file for complete search history.

(56) References Cited

U.S. PATENT DOCUMENTS 5,484,437 A * 1/1996 Michelson ............ A61F 2/4611
  606/279
5,573,537 A * 11/1996 Rogozinski ........ A61B 17/7092
  606/80

(Continued)

FOREIGN PATENT DOCUMENTS

CN  104997549 A  10/2015
CN  105848606 A  8/2016
(Continued)

*Primary Examiner* — Christian A Sevilla
(74) *Attorney, Agent, or Firm* — Cheng-Ju Chiang (57) ABSTRACT

An orthopedic implantation operation system includes a power drill mechanism and a linear advancing mechanism. The linear advancing mechanism includes a linear motor; the linear motor is connected with the power drill mechanism to drive the power drill mechanism to make a linear reciprocating motion to realize the advancement motion of the surgical tool. The present invention provides the driving force of the linear reciprocating motion of the power drill mechanism through a linear advancing mechanism, and combines with a power drill mechanism to clamp surgical tools such as a guide pin, reamer, tap and a vertebral pedicle screw, etc. so as to realize the operation of orthopedic implantation. Compared with artificial orthopedic implantation operations, the operation is stable, the impact on the human body is small, and the operation efficiency and accuracy of orthopedic implantation operations are higher, avoiding accidental injuries that may be caused by manual orthopedic implantation.

19 Claims, 4 Drawing Sheets

(51) Int. Cl.
*A61B 34/20* (2016.01)
*A61B 17/00* (2006.01)
*A61B 90/00* (2016.01)

(52) U.S. Cl.
CPC ............ *A61B 2017/00017* (2013.01); *A61B 2017/00398* (2013.01); *A61B 2017/00477* (2013.01); *A61B 2034/2057* (2016.02); *A61B 2090/064* (2016.02); *A61B 2090/066* (2016.02)

(56) References Cited

U.S. PATENT DOCUMENTS

| | | | |
|---|---|---|---|
| 6,063,088 A * | 5/2000 | Winslow | A61F 2/4611 |
| | | | 606/279 |
| 2005/0096684 A1* | 5/2005 | Farrow | A61B 17/32002 |
| | | | 600/170 |
| 2006/0181157 A1 | 8/2006 | Qiu | |
| 2007/0083209 A1* | 4/2007 | Schenberger | A61B 17/142 |
| | | | 606/82 |
| 2008/0119860 A1* | 5/2008 | McCarthy | A61B 17/15 |
| | | | 606/82 |

FOREIGN PATENT DOCUMENTS

| | | | |
|---|---|---|---|
| CN | 105997253 A | 10/2016 | |
| CN | 106170266 A | 11/2016 | |
| CN | 205903308 U | 1/2017 | |
| CN | 107773305 A | 3/2018 | |
| CN | 108742847 A | 11/2018 | |
| CN | 215018667 U | 12/2021 | |

* cited by examiner

ORTHOPEDIC IMPLANTATION OPERATION SYSTEM

CROSS REFERENCE TO RELATED APPLICATIONS

The present invention claims benefit of Chinese Application No. 202121629860.3, filed on Jul. 16, 2021, the disclosure of which is incorporated by reference herein. The Chinese Application was filed in Chinese.

TECHNICAL FIELD

The invention relates to the technical field of medical devices, in particular to an orthopedic implantation operation system.

BACKGROUND

Orthopedic implantation surgery, such as vertebral pedicle screw implantation surgery is a very common surgery. Vertebral pedicle screw plays an important role in the treatment of spinal trauma reduction and deformity correction. The key to the success of the vertebral pedicle screw internal fixing surgery is whether the screw can be accurately inserted through the vertebral pedicle without damaging the nerve vertebral body.

Currently, there is no automatic or semi-automatic vertebral pedicle screw placement tool that can be directly used for orthopedic surgical robots. The currently known orthopedic surgical robots are only used for navigation and positioning to the lesion, and the screw is manually placed by the doctor, or use an orthopedic electric drill to manually insert the screw. When the doctor manually taps and inserts the screw, the doctor needs to exert a lot of physical effort. In addition, due to the high hardness of cortical bone, doctors often need to use hammers and other tools to strike when manually reaming. This operation causes relatively large impact on the human body and is prone to accidental injuries. In addition, when screwing the screw manually, the final tightening torque cannot be effectively controlled. When using a low-speed bone drill for tapping and screw placement, the doctor lacks the feel of manual screwing, and it is difficult to judge whether the screw is in place. Although setting a navigation marker on the end of tools such as tapping tools and low-speed bone drills can track the position of the tip of the tool in the bone in real time, but due to human response and physiological fatigue, there will be a delay, resulting in inaccurate depth.

Therefore, there is a need to provide an orthopedic implantation operation system, which is convenient and easy to operate, provides precise placement of screw, can improve surgical efficiency, and reduce surgical injuries.

SUMMARY OF THE INVENTION

An object of the present invention is to provide an orthopedic implantation operation system that is convenient and easy to operate and precise in the operation position.

In order to achieve the object of the present invention, the following technical solution is provided. An orthopedic implantation surgical system, includes a power drill mechanism for installing a surgical tool and driving the surgical tool to rotate, and a linear advancing mechanism, the linear advancing mechanism including a linear motor; the linear motor being connected with the power drill mechanism to drive the power drill mechanism to make a linear reciprocating motion to realize an advancement motion of the surgical tool.

In some embodiments, the power drill mechanism includes a linear motor which drives the surgical tool to rotate; the linear advancing mechanism includes a bottom plate and a linear guide rail, and the linear motor and the linear guide rail are installed on the bottom plate; the linear advancing mechanism also includes a moving seat which is connected with the power drill mechanism and a rotor of the linear motor, and the rotor of the linear motor drives the moving seat, thereby driving the power drill mechanism to perform linear reciprocating motion; the linear motor of the power drill mechanism is installed on a motor mounting seat; the motor mounting seat and the moving seat are connected by a guide shaft, and the motor mounting seat and the moving seat jointly move linearly and reciprocally along the linear guide rail.

In some embodiments, the orthopedic implantation operation system further includes a pressure sensor for detecting the resistance of the surgical tool during the advancement process; the pressure sensor is installed between the linear advancing mechanism and the power drill mechanism; the power drill mechanism includes a clamping mechanism for clamping an orthopedic implantation surgical tool; a motor output shaft of the power drill mechanism is connected to a torque sensor, and the rotation output of the motor is transmitted to the surgical tool clamped by the clamping mechanism through the torque sensor; the torque sensor measures the torque during orthopedic implantation surgery; the power drill mechanism is provided with a limit switch to limit the front and rear limit positions of the power drill mechanism for linear reciprocating motion.

In some embodiments, the clamping mechanism includes a speed reducer and a quick-release joint connected with the speed reducer, and the quick-release joint clamps the surgical tool in a detachable manner; the surgical tool is connected with an output shaft of the speed reducer; the rotation output of the motor of the power drill mechanism is transmitted to the speed reducer, and the output shaft of the speed reducer drives the rotation of the surgical tool; a sliding block is provided on the linear guide rail, and the sliding block slides along the linear guide rail; the moving seat is connected with the sliding block, and the moving seat and the sliding block slide together along the linear guide rail; the pressure sensor is installed on the moving seat; the limit switch includes a pair of photoelectric switches and a pair of corresponding sensing sheets; the pair of photoelectric switches are respectively installed on both sides of the bottom plate, and the pair of sensing sheets are respectively installed on the moving seat and the motor mounting seat, and the front and rear positions of the power drill mechanism during linear reciprocating motion are restricted, through the cooperation of the corresponding sensor sheet and the corresponding photoelectric switch; the orthopedic implantation operation system includes a control circuit; the control circuit is electrically connected with the linear motor and the motor of the power drill mechanism to control the operation of the motor; the control circuit is connected with a pressure sensor to obtain sensor information; the control circuit is connected with the torque sensor to obtain the torque sensor information; the control circuit is electrically connected with the limit switch to obtain limit switch information and control the operation of the motor.

In some embodiments, the linear guide rail includes two sliding blocks; the moving seat is installed on one sliding block of the linear guide rail; the motor mounting seat is installed on the other sliding block; the linear advancing mechanism includes a pair of the linear guide rails; two sides of the moving seat are respectively mounted on corresponding sliding blocks of the pair of linear guide rails, and two sides of the motor mounting seat are respectively mounted on the rest of the sliding blocks of the pair of linear guide rails; the power drill mechanism further includes an optionally used speed increaser, the speed reducer is connected with a drill chuck, and the drill chuck is used for clamping the surgical tool; a secondary output shaft of the speed reducer is connected with an input shaft of the speed increaser to realize speed increase; one end of a spindle of the torque sensor is connected to the output shaft of the motor of the power drill mechanism through an adapter, and the other end thereof is connected to the input shaft of the speed reducer such that the rotating motion of the motor is transmitted to the speed reducer through the torque sensor to drive the surgical tool to rotate; the motor drives the spindle of the torque sensor to rotate, and the torque is detected by the torque sensor; the moving seat is provided with a shaft hole; the other end of the spindle of the torque sensor passes through the shaft hole in the moving seat and is connected with the input shaft of the speed reducer.

In some embodiments, when the orthopedic implantation surgical system implements the guide pin implantation, the speed increaser and speed reducer are sequentially connected to achieve high-speed output; when performing surgical operations such as reaming, tapping and screw placement, the speed reducer is used to achieve low-speed and high-torque output; the linear advancing mechanism also includes a speed reducer mounting seat for supporting the speed reducer; the linear advancing mechanism further includes a bearing; the guide shaft passes through the bearing, and two ends of the guide shaft are respectively connected with the motor mounting seat and the moving seat; the bearing reciprocates linearly along the guide shaft; the speed reducer mounting seat is connected to the bearing, and linearly reciprocates with the bearing; the linear advancing mechanism further includes a sensor fixing block, the sensor fixing block is respectively fixed with the pressure sensor and the speed reducer mounting seat, and the pressure detection is realized by the relative movement of the speed reducer mounting seat and the moving seat.

In some embodiments, a pair of said guide shafts are respectively connected to both sides of the motor mounting seat and the moving seat, and each guide shaft is slidably sleeved with a bearing; the surgical tool includes one or more of a guide pin, a reamer, and a bone screw connected to an extender; the orthopedic implantation operation system also includes a guide pin fixing mechanism that is selectively used; the guide pin fixing mechanism includes a fixing support, a connecting rod mounting block, a pair of clamping blocks, and at least a pair of connecting rods; the fixing support is installed on the bottom plate; the connecting rod mounting block is installed on the fixing support, or the fixing support and the connecting rod mounting block are of an integral structure; one end of the connecting rod is movably connected to the connecting rod mounting block, and the other end is connected to the clamping block; a pair of the clamping blocks are locked together by a fastener, and the guide pin is clamped and fixed; in a surgical operation in which a guide pin is used for guiding, the guide pin fixing mechanism is used to clamp and fix the guide pin; the speed reducer mounting seat is a cover structure, which covers the bottom plate and the rotor of the linear motor; the torque sensor connecting seat, the moving seat, and the motor mounting seat are housed in the cover structure; the speed reducer is located at a front end of the cover structure and is supported by the sensor fixing block.

In some embodiments, the guide pin fixing mechanism includes a pair of long connecting rods and a pair of short connecting rods; corresponding ends of the pair of long connecting rods are respectively rotatably mounted on both sides of the connecting rod mounting block; corresponding ends of the pair of short connecting rods are respectively rotatably mounted on both sides of the connecting rod mounting seat; the other end of one of the long connecting rods and the other end of the corresponding one of the short connecting rods are respectively connected and fixed to a clamping block; a manually operated screw locks the pair of clamping blocks together, and the guide pin is clamped between the pair of clamping blocks; the clamping blocks are locked to each other and are located on the top of the speed reducer mounting seat and at the same time in a length direction of the guide pin.

In some embodiments, the orthopedic implantation operation system further includes a housing and a cross-laser system; the cross-laser system is installed at a front end of the housing; the orthopedic implantation operation system further includes a control circuit, and a computing device or a control center; the control circuit is electrically connected to the computing device and/or the control center, or the control circuit is provided in the computing device and/or the control center; the orthopedic implantation operation system further includes a binocular camera installed at a front end of the linear advancing mechanism and connected to the computing device or control center; the power drill mechanism is provided with a navigation surface, and a visible light visual recognition tracking pattern adapted to the binocular vision camera is installed on the navigation surface; tracking and monitoring is achieved by tracking the navigation surface with the binocular camera; the orthopedic implantation operation system further includes a guide tube mechanism for selective use; the guide tube mechanism is installed at a front end of the bottom plate; the guide tube mechanism includes a guide tube, a guide tube locking seat and a guide tube seat; the guide tube passes through a through hole of the guide tube locking seat and is installed in the guide tube locking seat; the guide tube locking seat is detachably installed on the guide tube seat; the guide tube mechanism further includes an upper and lower adjusting seat and an adjusting seat; the guide tube seat is installed on the upper and lower adjusting seat, the upper and lower adjusting seat is installed on the adjusting seat, and the adjusting seat is installed on the bottom plate; the up and down adjusting seat can move up and down relative to the adjusting seat to adjust the height and position.

In some embodiments, the orthopedic implantation surgical system includes a surgical robot, the computing device and/or control center is arranged on the surgical robot or arranged outside of the surgical robot, and the surgical robot controls the work of the linear advancing mechanism and the power drill mechanism through an interface and a sensor.

Compared with the prior art, the present invention has the following advantages.

The present invention provides the driving force of the linear reciprocating motion of the power drill mechanism through a linear advancing mechanism, and combines with a power drill mechanism to clamp surgical tools such as a guide pin, reamer, tap and a vertebral pedicle screw, etc. so as to realize the operation of orthopedic implantation. Compared with artificial orthopedic implantation operations, the operation is stable, the impact on the human body is small, and the operation efficiency and accuracy of orthopedic implantation operations are higher, avoiding accidental injuries that may be caused by manual orthopedic implantation.

Further, the orthopedic implantation operation system of the present invention is also provided with a pressure sensor to complete real-time pressure measurement, which can measure the resistance of the surgical tool during the advancement process in each process of the orthopedic implantation surgery. A torque sensor is provided between the power drill driving device and the surgical tool clamping mechanism, through which the torque of the vertebral pedicle screw can be accurately measured during the entire insertion process, thereby intelligently judging whether the bone screw has been placed in place, and avoiding loosening of bone screws due to lack of tightening, so as to improve the success rate and accuracy of the operation.

The orthopedic implantation surgical system of the present invention can also be fixed to an orthopedic surgical robot arm through the installation interface. The parameters of each link of the screw placement operation can be accurately controlled according to the preoperative surgical planning, reducing the deviation caused by manual operation. This ensures the accuracy of the operation and reduces the labor intensity of the doctor at the same time.

Further, the present invention combines the orthopedic implantation operation system with the binocular vision system and the control center to form a complete surgical operating system, and realizes the intelligent orthopedic implantation operation. It can also track the operating conditions of the intelligent orthopedic implantation operation system through the binocular vision system, perform tracking and monitoring, improve the accuracy of the orthopedic implantation operation, and reduce the operation risk.

DETAILED DESCRIPTION

The present invention provides an orthopedic implantation operation system, including a power drill mechanism 1 and a linear advancing mechanism 2 connected with the power drill mechanism 1 and used to generate linear reciprocating motion. The power drill mechanism 1 includes a power drill driving device 12 and a clamping mechanism 10 connected and driven by the power drill driving device. The clamping mechanism 10 is used to clamp an orthopedic implantation surgical tool 6, such as a guide pin 60, a reamer 61, a tap, and a bone screw 62 installed by an extender.

Specifically, the power drill driving device 12 may adopt a driving motor. The present invention provides the driving force of the linear reciprocating motion of the power drill mechanism through a linear advancing mechanism, and combines with the power drill driving device to control the clamping mechanism, thereby realizing orthopedic implantation operation, in order to improve the efficiency of the operation and the accuracy of the orthopedic implantation operation, to avoid the accidental injury that may be caused by the previous free-hand orthopedic implantation operation.

Please refer to FIGS. 1-5. In this embodiment, an orthopedic implantation surgical system includes: a power drill mechanism 1, a linear advancing mechanism 2, a surgical tool 6, an optional guide pin fixing mechanism 7, and a cross-laser system 8, an optional guide tube mechanism 3, and a binocular camera 9. The orthopedic implantation operation system of the present invention is often used as an operating device for orthopedic screw implantation surgery.

The power drill mechanism 1 is connected to the linear advancing mechanism 2, and the linear advancing mechanism 2 generates linear reciprocating motion, and drives the power drill mechanism 1 to perform linear reciprocating motion. The power drill mechanism 1 includes a power drill driving device 12 and a surgical tool clamping mechanism 10 connected with the power drill driving device 12. The clamping mechanism 10 is equipped with a tool for orthopedic implantation surgery, that is, a surgical tool 6. The power drill driving device 12 drives the surgical tool 6 to rotate. The power drill driving device 12 is generally a motor, and the power drill mechanism 1 further includes a motor mounting seat 13 on which the motor is mounted. The motor mounting seat 13 is connected to the linear advancing mechanism 2, so that the linear advancing mechanism 2 drives the power drill mechanism 1 to perform linear movement, and the surgical tool is moved towards the surgical site.

Specifically, the linear advancing mechanism 2 includes a bottom plate 29, a linear motor 20 installed on the bottom plate 29, a pair of linear guide rails 2, a moving seat 23, a pair of photoelectric switches 230 and a sensing sheet 231. There are two sliding blocks 210, and the two sliding blocks 210 slide relative to the linear guide rail 21 without departing from the linear guide rail 21. The moving seat 23 is respectively connected with the linear motor 20 and the linear guide rails 21, and the moving seat 23 is driven by the linear motor 20 to generate linear reciprocating relative motion. Specifically, the moving seat 23 is installed on a mover 201 of the linear motor, and is driven by the mover 201 to perform linear motion. At the same time, the moving seat 23 is installed on the sling blocks 210 and slides along the guide rails 21 together with the sliding blocks 210. In this embodiment, a stator 200 of the linear motor is arranged between a pair of linear guide rails 21. The linear motor 20 can be a flat-plate linear motor or a U-slot linear motor. The linear guide rail 21 is fixedly installed with the bottom plate 29, and the linear motor 20 is installed on the bottom plate 29.

The pair of photoelectric switches 230 are installed on both sides of the bottom plate 29, and the pair of sensing sheets 231 are respectively installed on the moving seat 23 and the motor mounting seat 13. Through the cooperation of the corresponding sensing sheet 231 and the corresponding photoelectric switch 230, the front and rear positions of the power drill mechanism 1 during linear reciprocating motion are restricted from exceeding the limit, so as to avoid mechanical failure. The photoelectric switches 230 may adopt other limit switches to detect and limit the limit position of the power drill mechanism 1. The photoelectric switch 230 may be an infrared light sensor, and may include an infrared receiving module and an infrared transmitting module. When the moving seat 23 or the motor mounting seat 13 moves to move the sensing sheet 231 to the photoelectric switch 230, the infrared signal is blocked. The information of the photoelectric switch is transmitted to a control main board or a control center to control the on or off of the linear motor.

The power drill mechanism 1 is installed on the moving seat 23 and moves together with the moving seat 23. The motor mounting seat 13 of the power drill mechanism 1 is connected with the moving seat 23 of the linear advancing mechanism 2, specifically connected by a guide shaft 17. In this embodiment, the guide shaft 17 is relatively slidably sleeved with a bearing 18, and the two ends of the guide shaft 17 are respectively connected to the motor mounting seat 13 and the linear advancing mechanism 2, so that the relative position of the motor mounting seat 13 and the linear advancing mechanism 2 is fixed.

The moving seat 23 is mounted on a sliding block 210 of the linear guide rail 21, and the motor mounting seat 13 is mounted on another sliding block 210 of the linear guide rail 21, and can perform linear reciprocating relative movement along the linear guide rail 21. The bearing 18 is installed on the guide shaft 17, and the bearing 18 can make relative movement along the guide shaft 17. The motor mounting seat 13 is fixed with the moving seat 23 through the guide shaft 17 and performs linear reciprocating motion along the linear guide rail 21 together. The bearing 18 is located between the motor mounting seat 13 and the moving seat 23, and is connected in series by the guide shaft 17, and the motor mounting seat 13 and the moving seat 23 drive the bearing to make a linear reciprocating motion together. Axle holes (not shown) are respectively opened in the motor mounting seat 13 and the moving seat 23, and two ends of the guide shaft 17 is installed in these shaft holes respectively. A through hole is provided in the bearing 18, and the guide shaft 17 passes through the through hole.

The linear advancing mechanism 2 further includes a pressure sensor 26 fixed on the moving seat 23. At the same time, the pressure sensor 26 is installed on the power drill mechanism 1 through a sensor fixing block 260, and the pressure sensor 26 is located between the linear advancing mechanism 2 and the power drill mechanism 1. Pressure detection can be achieved by the relative movement or interaction force between the linear advancing mechanism 2 and the power drill mechanism 1. The pressure sensor completes the real-time pressure measurement, and can measure the resistance of the surgical tools in the various procedures of the orthopedic implantation operation during the advancement process, so as to avoid the occurrence of surgical accidents. The power drill mechanism 1 includes a speed reducer 11 and a speed reducer mounting seat 16, and the speed reducer 11 is used to install and clamp the surgical tool 6. The speed reducer mounting seat 16 is fixed on the bearing 18 and can perform linear reciprocating motion along with the bearing 18. The sensor fixing block 260 is fixed to the pressure sensor 26 and the speed reducer mounting seat 16 respectively, and pressure detection can be realized by the relative movement of the speed reducer mounting seat 16 and the moving seat 23. In this embodiment, the speed reducer mounting seat 16 is a cover structure, which covers the moving seat 23, a torque sensor 15 and the motor mounting seat 13. A groove (not shown) is provided on the bottom edge of the speed reducer mounting seat 16, and the groove is in a tight fit with the bearing 18, and the bearing 18 is located between the sensor fixing block 260 and the motor mounting seat 13. The guide shaft 17 passes through the bearing 18, and both ends of the guide shaft 17 are respectively connected to the sensor fixing block 260 and the motor mounting seat 13 at the front and rear of the bearing, so as to slide together as a whole.

The power drill mechanism 1 further includes the aforementioned torque sensor 15, a servo motor 12 (the driving device and the motor are all indicated by a reference numeral 12), and an adapter 14. The torque sensor 15 is mounted on the moving seat 23, and the servo motor 12 is mounted on the motor mounting seat 13. The servo motor 12 is connected to the torque sensor 15 through the adapter 14, so that the servo motor 12 can drive a spindle of the torque sensor to rotate. The spindle of the torque sensor rotates, thereby driving the corresponding surgical tool 6 clamped in the speed reducer 11 to rotate, so as to perform related surgical operations such as channel establishment, hole reaming, tapping or screw placement. In addition, the torque sensor 15 can detect the magnitude of the torque in real time. The torque sensor 15 can accurately measure the torque during the entire screw placement operation, thereby intelligently judging whether the surgical tool, such as a bone screw, has been placed in place, and avoiding loosening of bone screws in the surgical site (such as vertebral pedicle) due to lack of tightening, so as to improve the success rate and accuracy of the operation.

The clamping mechanism 10 of the power drill mechanism 1 is used to clamp the surgical tool 6. The clamping mechanism 10 includes the speed reducer 11, which is mounted on the speed reducer mounting seat 16. The input shaft of the speed reducer 11 is connected to the torque sensor 15, and the servo motor 12 transmits the rotational movement to the speed reducer 11 through the torque sensor 15. The speed reducer 11 is connected with a quick-release joint 110 for the detachable surgical tool 6. The quick-release joint 110 may adopt a matching structure of a spring, a steel ball, and a sleeve, so that the surgical tool 6 can be easily and quickly removed.

The orthopedic implantation operation system of the present invention also includes a speed increaser 19 which cooperates with the speed reducer 11 to meet the different requirements of the rotational speed in the surgical operations such as guide pin insertion, reaming, tapping, and screw placement.

Figure 1:
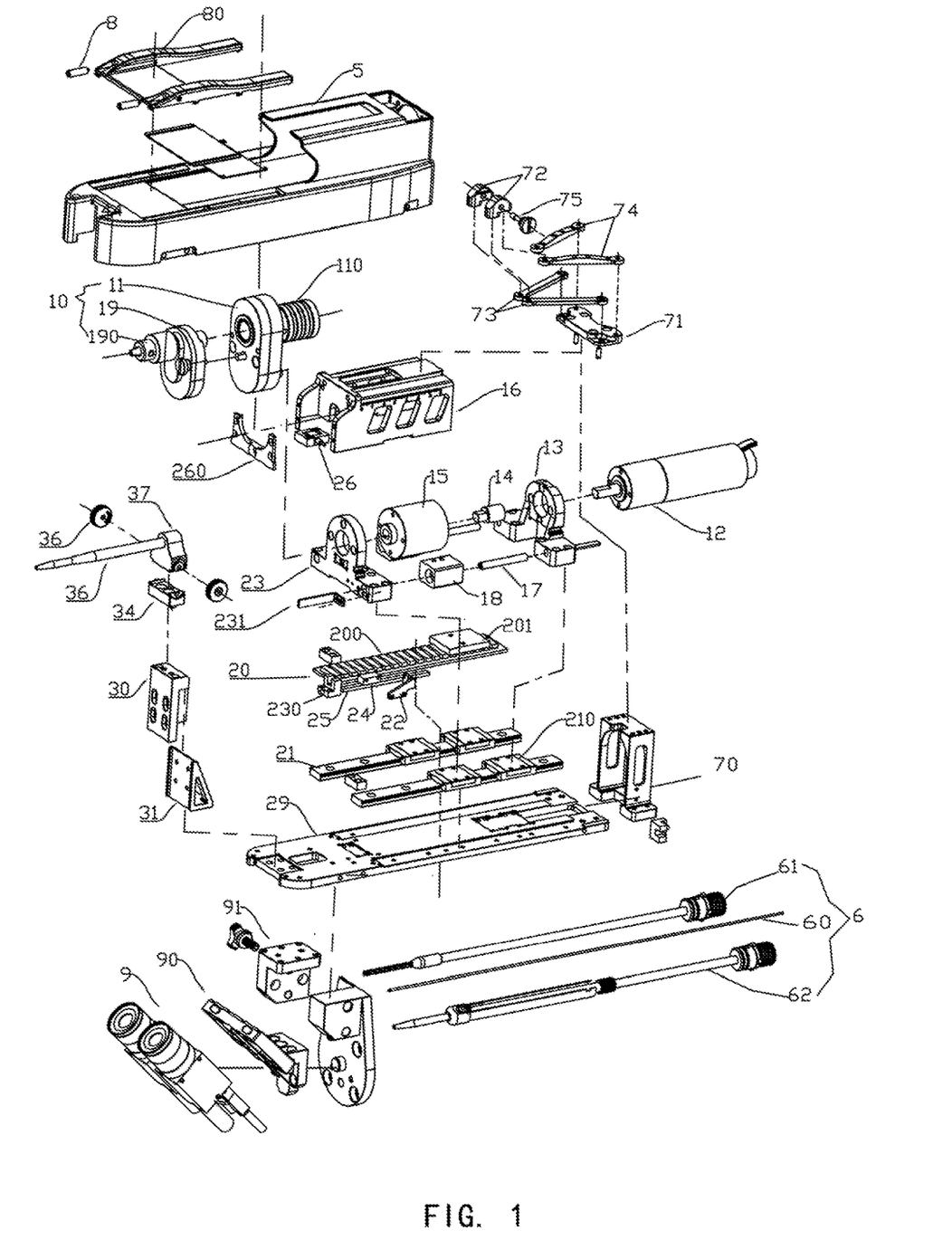
FIG. 1 is an exploded view of an orthopedic implantation operation system according to an embodiment of the present invention.
Figure 2:
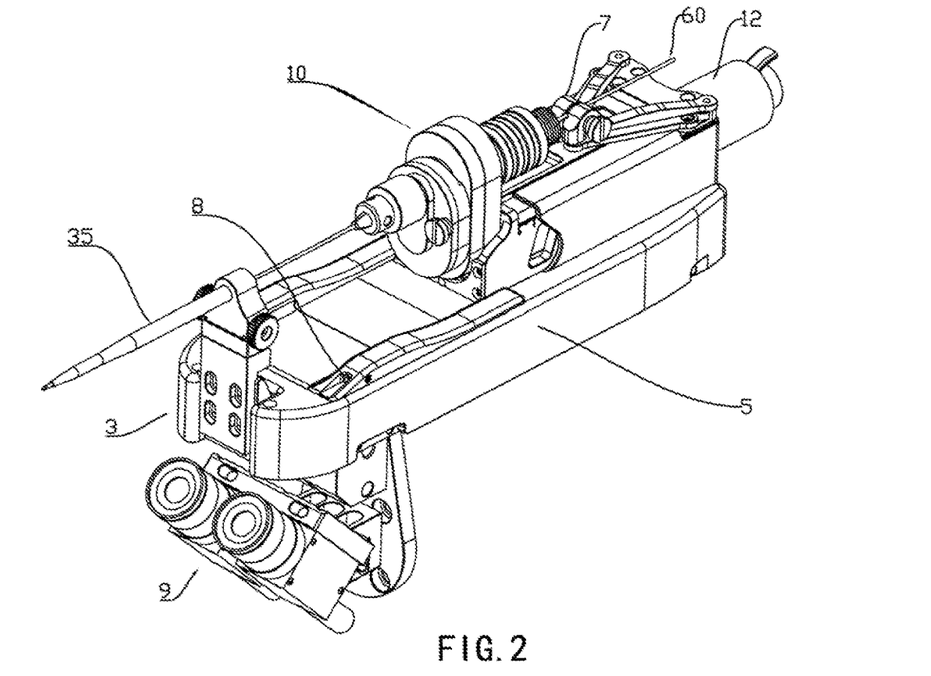
FIG. 2 is a perspective view of an orthopedic implantation operation system according to an embodiment of the present invention.
Figure 3:
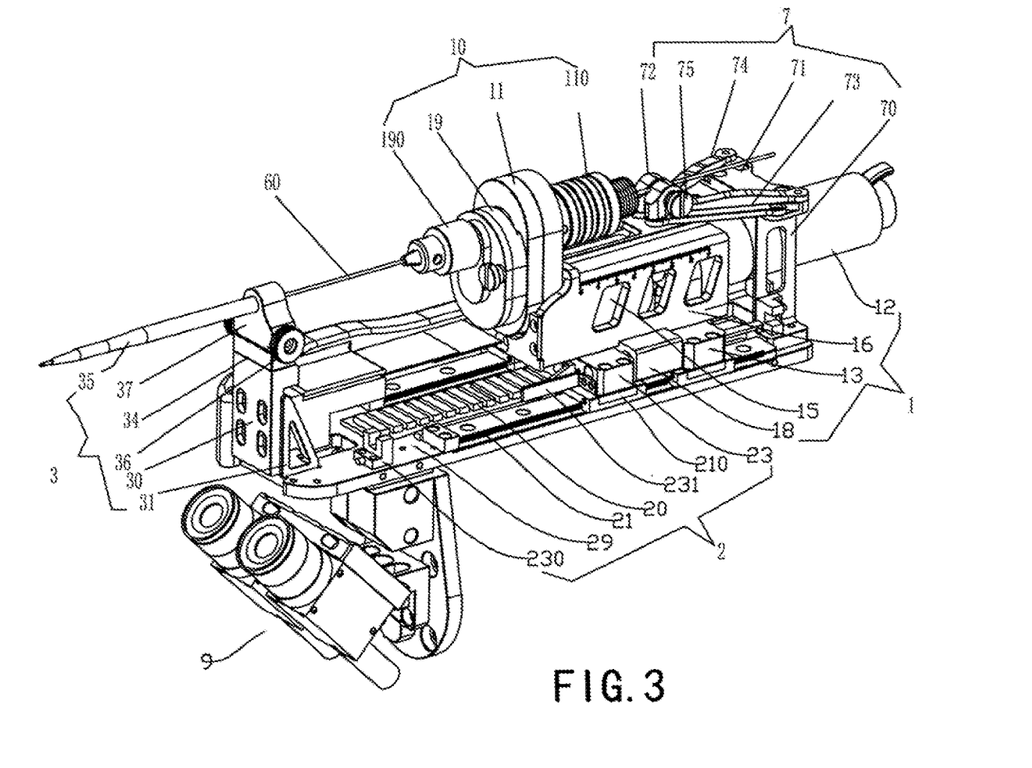
FIG. 3 is a perspective view of the orthopedic implantation operation system according to an embodiment of the present invention with a part of an outer shell removed.
Figure 4:
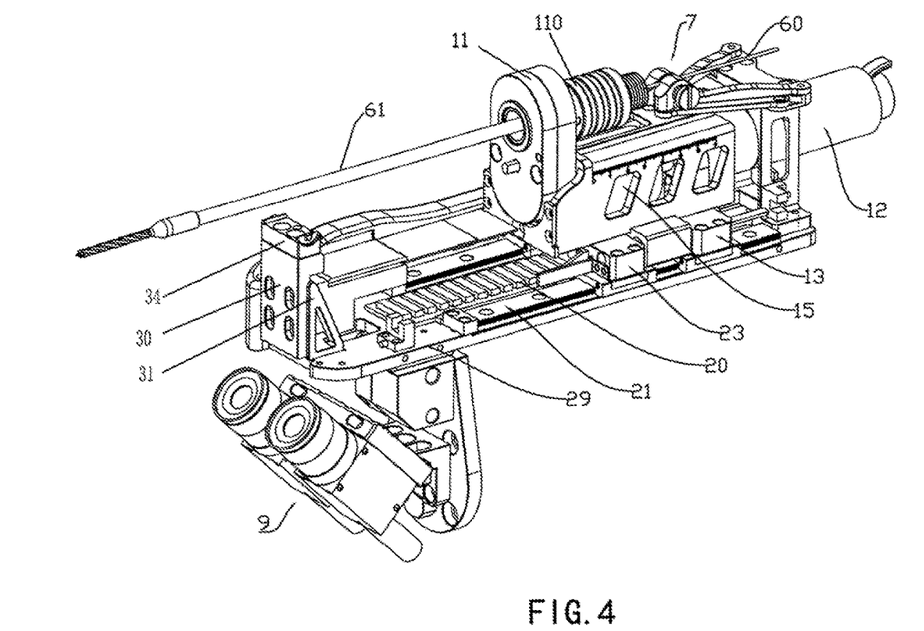
FIG. 4 is a perspective view of the orthopedic implantation operation system of an embodiment of the present invention when a reamer is clamped.
Figure 5:
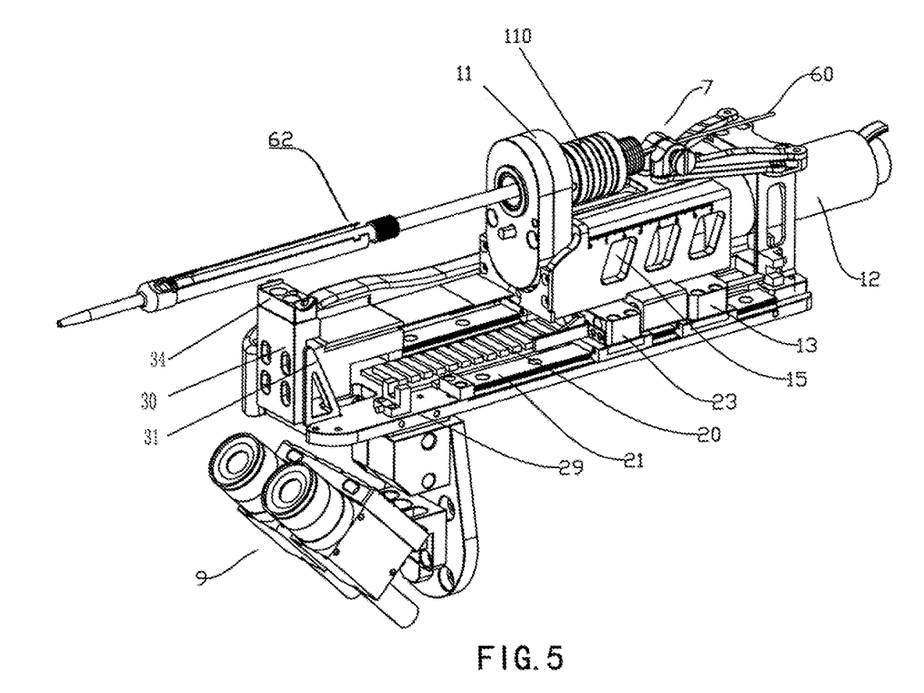
FIG. 5 is a perspective view of the orthopedic implantation surgical system clamping a screw-placing surgical tool according to an embodiment of the present invention.

Here, when the guide pin 60 is inserted, the speed increaser 19 and the speed reducer 11 are connected in sequence to achieve high-speed output. When performing reaming, tapping and screw placement operations, only the speed reducer 11 is required to achieve low-speed and high-torque output. At this time, the speed increaser 19 needs to be removed, and the quick-release joint 110 behind the speed reducer 11 separately clamps the tools for reaming, tapping or screw placement operations. Referring to FIGS. 2-3, when the guide pin 60 is inserted, the speed increaser 19 and the speed reducer 11 are connected in sequence to achieve high-speed output. Referring to FIGS. 4-5, when reaming, tapping and screwing, only the speed reducer 11 may be used to achieve low-speed and high-torque output, and the speed increaser 11 may not be used at this time.

Specifically, when the guide pin 60 is inserted, the speed increaser 19 is connected to the speed reducer 11 in order to achieve high-speed output. At this time, a drill chuck 190 is used to clamp the guide pin and install it on the speed increaser 19. The speed increaser 19 is coupled with the speed reducer 11, and s secondary output shaft of the speed reducer 11 is connected with an input shaft of the speed increaser 19 to realize the effect of increasing the speed. The speed increaser 19 is provided with the drill chuck 190, the speed increaser 19 and its drill chuck 190 clamp the guide pin forward, and the speed reducer 11 and the quick-release joint 110 clamp the surgical tools for reaming, tapping or screwing backward. The quick-release joint 110 is coaxially connected with a primary output shaft of the speed reducer 11, and the drill chuck 190 is coaxially connected with an output shaft of the speed increaser 19. The speed reducer 11 is connected with the power drill driving device 12. The primary output shaft of the speed reducer 11 is coaxial with the output shaft of the speed increaser 19. Therefore, the orthopedic implantation tool 6 such as the guide pin 60 is connected with the primary output shaft of the speed reducer 11 and the output shaft of the speed increaser 19 respectively, and is clamped by the drill chuck 190. The primary output shaft of the speed reducer 11 and/or the output shaft of the speed increaser 19 drive the surgical tool 6 (guide pin 60) to rotate.

Referring again to FIGS. 4-5, the clamping mechanism 10 is a two-in-one multifunctional clamping mechanism for reaming/screw placement surgical tools. The clamping mechanism 10 includes a speed reducer 11 and a quick-release joint 110. The speed reducer 11 is connected to the torque sensor 15 and the power drill servo motor 12 respectively. The reamer 61 or the bone screw 62 connected to an extender can be quickly connected to the speed reducer 11 through the quick-release joint 110. The speed reducer 11 can be connected to the torque sensor 15 by screws, so that the servo motor 12 transmits the rotational movement to the speed reducer 11 through the torque sensor 15.

The surgical tool 6 is a tool for orthopedic implantation operations, and includes a guide pin 60, a reamer 61, and a bone screw 62 connected to the extender. The bone screw can be a vertebral pedicle screw. The surgical tool 6 is selected according to the operation plan of the orthopedic surgery.

The orthopedic implantation operation system of this embodiment also includes a guide pin fixing mechanism 7 for positioning the guide pin 60.

The guide pin fixing mechanism 7 includes a fixing support 70 and a connecting rod mounting block 71. The fixing support 70 is installed on the bottom plate 29, and the connecting rod mounting block 71 is installed on the fixing support 70. Specifically, the guide pin fixing mechanism 7 clamps and positions the tail of the guide pin 60, and the fixing support 70 is installed on the tail of the bottom plate 29 and fixed by fasteners such as screws. The connecting rod mounting block 71 is installed on the top of the fixing support 70 and is fixed by fasteners such as screws.

The guide pin fixing mechanism 7 further includes a clamping block 72, a short connecting rod 73, a long connecting rod 74, and a fastener such as a manually operated screw 75. In this embodiment, the corresponding ends of a pair of long connecting rods 74 is respectively installed on both sides of the connecting rod mounting block 71 so as to be rotatable around the mounting point (rotation shaft or hinge). The corresponding ends of a pair of short connecting rods 73 are respectively mounted on a connecting rod mounting seat 11 and can rotate around the mounting point (rotation shaft or hinge). A pair of clamping blocks 72 are respectively fixedly connected to the other end of the corresponding long connecting rod and short connecting rod. For example, the other ends of the long rod and the short rod are firmly connected to the bottom of the clamping block by fasteners such as screws. The two clamping blocks 72 are locked together by the manually operated screw 75 (or other fasteners), so that the guide pin 60 is clamped between the two clamping blocks 72. Surfaces of the two clamping blocks 72 facing each other form a guide pin groove together. When the two clamping blocks 72 are clamped, the guide pin groove is closed to clamp the guide pin 60 therein. In this embodiment, each clamping block 72 is rotatably connected to one side of the connecting rod mounting block 71 through the corresponding ends of the long connecting rod 74 and the short connecting rod 73 respectively arranged up and down. The bottom of the clamping block 72 forms a step, thereby fixing to the other ends of the long rod 74 and the short rod 73 in the up and down direction. A fastener such as the manually operated screw 75 locks the two clamping blocks 72 and is located on a top surface of the speed reducer mounting seat 16. Each clamping block 72 can also be rotatably connected to the connecting rod mounting block 71 by the long connecting rod or short connecting rod.

The orthopedic implantation operation system of this embodiment includes a housing 5, which is mounted on a bottom plate 29, and contains the linear advancing mechanism 2 and some components of the power drill mechanism 1. The speed reducer 42 is installed on the speed reducer mounting seat 16 and extends upward to a certain height outside the top of the housing 5 to install the orthopedic surgical tool 6.

The orthopedic implantation operation system of the present invention includes a cross-laser system 8. The cross-laser system 8 is installed at a front end of the orthopedic implantation operation system. A front shell 80 fixes the cross-laser system 8 on a front end of the shell 5 to provide the doctor with an accurate position of the patient's skin incision.

The orthopedic implantation operation system of the present invention includes a guide tube mechanism 3, which includes a guide tube 35, a locking knob 36, a guide tube locking seat 37, a guide tube seat 34, an upper and lower adjusting seat 30 and an adjusting seat 31. The guide tube 35 passes through a mounting hole in the guide tube locking seat 37 and is installed in the locking seat 37. A fastener, such as the locking knob 36, detachably install the locking seat 37 on the guide tube seat 34, so as to facilitate the disassembly and assembly of the guide tube and the guide tube mechanism 37. Referring to FIGS. 4-5, the guide tube 35 is not required for reaming and orthopedic implantation operations, so the guide tube 35 and the guide tube locking seat 37 are removed here. The guide tube seat 34 is installed on the upper and lower adjusting seat 30, and the upper and lower adjusting seat 30 is installed on the adjusting seat 31. The height can be adjusted by the upper and lower adjusting seat, and the positioning can be realized by fasteners such as manually operated screws or pins. The adjusting seat 31 is installed on the bottom plate 29. The guide tube mechanism 3 is installed at the front end of the housing 5 and the bottom plate 29.

The orthopedic implantation operation system of the present invention includes a binocular camera 9, which is installed under the front end of the linear advancing mechanism through a binocular mounting seat 90. The binocular camera 9 is fixed to a lower side of the bottom plate 29 or a lower side of the linear guide rail 21 through a platform fixing seat 91. The binocular camera 9 is connected to a computing device or a control center, and can perform tracking identification and intraoperative monitoring. The computing device or control center may be a computing device or console set on the surgical robot or set outside the surgical robot, and is used to obtain information, perform information processing, and function control.

The present invention also provides a system, including the above-mentioned orthopedic implantation operation system, a binocular vision system, and a computing device or control center. The binocular vision system is connected to the computing device/control center. The computing equipment/control center includes a processor and a memory for obtaining information, data processing, and functional control of the orthopedic implantation surgical system. The binocular vision system includes a binocular camera 9 for spatial positioning of binocular vision, and the binocular camera 9 is connected to the computing device/control center.

In this embodiment, the linear advancing mechanism 2 can be implemented as follows: the linear guide rail 21 and the bottom plate 29 are fixedly installed, the bottom plate 29 is installed with the linear motor 20, and the relative position of the linear motor 20 and the linear guide rail 21 is fixed. The sliding block 210 is arranged on the linear guide rail 21 and can perform linear reciprocating relative movement along the linear guide rail 21, and the moving seat 23 is fixed on the sliding block 210. The linear motor 20 drives the moving seat 23 and the linear guide rail 21 to generate linear reciprocating relative motion. The precise positioning of the advancement movement of the moving seat 23 is realized by a grating ruler 25 and a reading head 24. The reading head 24 is installed on the moving seat 23 through a reading head mounting seat 22, and can also be installed on the power drill mechanism 1 (for example, installed on the motor mounting seat 13). The moving seat 23 is provided with a sensing sheet 231 which cooperates with the photoelectric switch 230 to limit the moving position of the moving seat 23. The sensing sheet 231 may also be installed on the power drill mechanism 1 (for example, installed on the motor mounting seat 13). The power drill mechanism 1 is installed on the moving seat 23. In other embodiments, the moving seat 23 is located inside a front end of the speed reducer mounting seat 16, and the motor mounting seat 13 is located inside a rear end of the speed reducer mounting seat 16. A sensing sheet 231 is provided on the moving seat 23 to cooperate with the photoelectric switch 230 to limit the forward movement position of the moving seat 23. A sensing sheet 231 is provided on the motor mounting seat 13 to limit the limit position of the motor mounting seat 13 in the backward movement. The front and rear limit switch components are provided to limit the front and rear limit positions of the power drill mechanism.

In this embodiment, the power drill drive source adopted by the power drill mechanism 1 is a power drill servo motor 12. A torque sensor 15 is provided between the power drill servo motor 12 and the clamping mechanism 10 of the orthopedic surgical tool. The torque sensor 15 can accurately measure the torque of the vertebral pedicle screw or orthopedic implant during the entire implantation process, thereby intelligently judging whether the screw or bone implant has been placed in place, thus avoiding loosening of screws in the vertebral pedicle due to lack of tightening, and pedicle fracture. The power drill servo motor 12 is mounted on the motor mounting seat 13, the clamping mechanism 10 is mounted on the moving seat 23, and the guide shaft 17 is connected between the moving seat 23 of the linear advancing mechanism 2 and the motor mounting seat 13. A bearing 18 is installed on the guide shaft 17, and the motor mounting seat 13 is installed on another sliding block 210 on the linear guide rail 21.

A pressure sensor 26 is arranged between the moving seat 23 of the power drill mechanism 1 and the linear advancing mechanism 2 to complete real-time pressure measurement. The pressure sensor 26 can measure the resistance of the surgical tool during each process of orthopedic implantation surgery, and avoid surgical accidents.

In this embodiment, the fixing support 70 of the guide pin fixing mechanism 7 is installed on the bottom plate 29. The clamping block 72 is respectively connected to the speed reducer mounting seat 16 through the long connecting rod 74 and the short connecting rod 73, and is located behind the speed reducer 11 and corresponds to the position of the quick-release joint 110. The fastener locks the two clamping blocks 72 together, thereby clamping the guide pin 60.

The surgical operation of bone screw placement generally includes the following steps: positioning, forming a bottom hole, tapping, and screw placement. The orthopedic implantation operation system of the present invention can also be used for orthopedic surgery operations for placing other implants. Conventional implants are bone screws, such as hollow vertebral pedicle screws.

The orthopedic implantation operation system of the present invention further includes a guide pin fixing mechanism 7. In surgical operations such as reaming, tapping, and screw placement using the guide pin 60 for guiding, the guide pin fixing mechanism 7 is used to clamp and fix the guide pin 60. A front end of the guide pin 60 is inserted into the guide tube 35. First, the guide pin 60 is inserted according to the surgical site and angle. Refer to FIGS. 2-3, the guide pin is used to determine the position and angle of vertebral pedicle screw placement, and to guide tools such as reamers, taps, and bone screws connected to the extender. Then use the reamer 61, and referring to FIG. 4, the reamer 61 follows the guide pin for reaming the surgical site. Finally, the bone screw 62 connected to the extender is used instead, and the bone screw 62 is inserted along the guide pin 60, as shown in FIG. 5. The guide tube 35 is installed on the guide tube seat 34 by the guide tube locking seat 37, or removed from the guide tube seat 34. During the insertion of the guide pin 60, the guide pin fixing mechanism 7 does not participate in the work.

The orthopedic implantation operation system also includes a control circuit, which is used to control the operation of the orthopedic implantation surgery and detect the situation of the orthopedic implantation surgery at the same time. Specifically, the control circuit is connected to the control center/computing equipment through RSS485 or CAN communication, and controls various movements of the tool according to the preoperative planning. The orthopedic implantation operation system also includes an installation interface, through which the orthopedic implantation operation system can be installed on the mechanical arm of the orthopedic surgical robot to realize intelligent and semi-automatic orthopedic implantation surgery.

Figure 6:
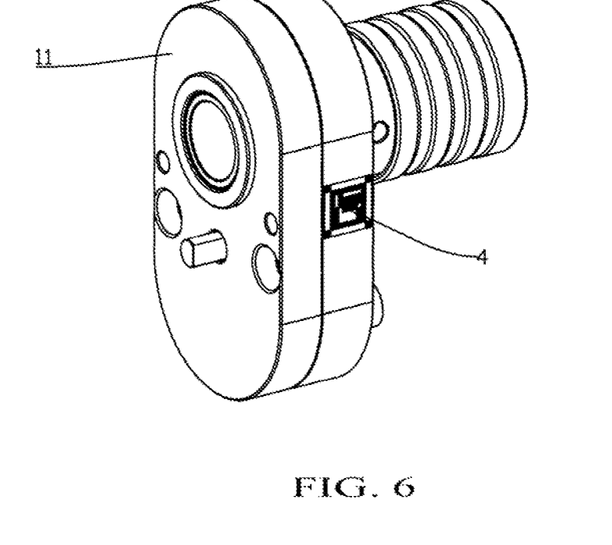
FIG. 6 is a structural schematic diagram of the navigation surface set on a main body of a speed reducer.
Figure 7:
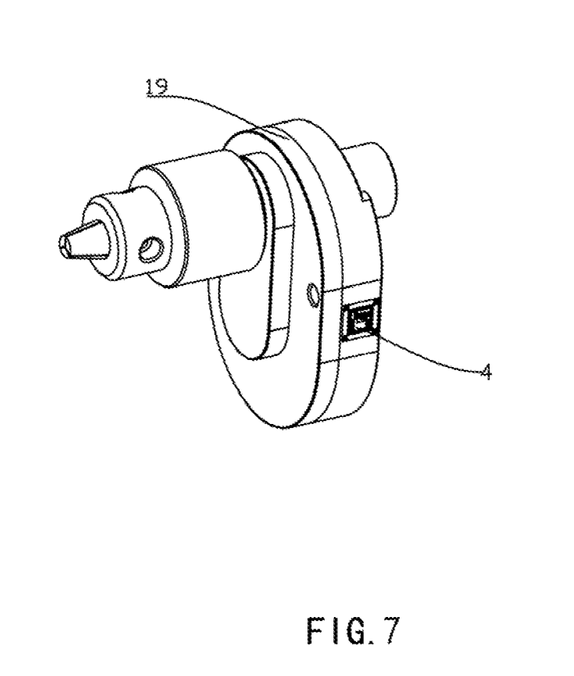
FIG. 7 is a structural schematic diagram of the navigation surface set on a speed increaser.

Referring to FIGS. 6-7, the clamping mechanism of the power drill mechanism of the orthopedic implant surgical system of the present invention can be provided with a navigation surface 4, and the navigation surface can be provided on the body of the speed reducer 11. The navigation surface 4 is provided with a visible light visual recognition tracking pattern adapted to the binocular vision system. The binocular vision system is used to track the navigation surface of the intelligent orthopedic implant operation system for tracking and monitoring. The navigation surface 4 can also be arranged on the body of the speed increaser 19.

The structures or components in the above embodiments can be combined or replaced with each other to obtain other embodiments. This is still the scope of the present invention, and the specific structure and working principle are not described here.

The present invention provides the driving force of the linear reciprocating motion of the power drill mechanism through the linear advancing mechanism, and combines the power drill driving device to control the clamping mechanism. The clamping mechanism mainly includes a speed reducer 11 and a quick-release joint 110. The quick-release joint 110 is used to clamp the guide pin, reamer, tap or bone screw (such as vertebral pedicle screw) connected to the extender required in the operation, so as to realize the orthopedic implantation operation. The orthopedic implantation operation system of the present invention is used for orthopedic implantation operations. Compared with artificial orthopedic implantation operations, the operation is stable, the impact on the human body is small, and the operation efficiency and accuracy of orthopedic implantation operations are higher, avoiding accidental injuries that may be caused by manual orthopedic implantation.

The foregoing are only preferred embodiments of the present invention, and the protection scope of the present invention is not limited thereto. Any equivalent transformation based on the technical solution of the present invention shall fall within the protection scope of the present invention.

What is claimed is:

1. An orthopedic implantation operation system, comprising:
    a control circuit;
    a power drill mechanism for installing a surgical tool and driving the surgical tool to rotate, comprising a motor electrically connected with the control circuit; and
    a linear advancing mechanism including:
        a linear motor electrically connected with the control circuit;
        a linear guide rail; and
        a moving seat connected with the linear motor;
    wherein the moving seat of the linear motor is connected with the power drill mechanism; wherein the linear motor is capable of driving the moving seat to cause the power drill mechanism to perform a linear reciprocating motion to obtain an advancement motion of the surgical tool; wherein the motor of the power drill mechanism is installed on a motor mounting seat; and wherein the motor mounting seat and the moving seat are connected and are movable back and forth along the linear guide rail.

2. The orthopedic implantation operation system according to claim 1, further comprising a bottom plate; wherein the linear motor and the linear guide rail are installed on the bottom plate; and wherein the motor mounting seat and the moving seat are connected by a guide shaft.

3. The orthopedic implantation operation system according to claim 2, wherein: a sliding block is provided on the linear guide rail, and the sliding block is slidable along the linear guide rail; the moving seat is connected with the sliding block, thereby the moving seat and the sliding block are slidable together along the linear guide rail.

4. The orthopedic implantation operation system according to claim 3, wherein: the linear guide rail is provided with two sliding blocks; the moving seat is installed on one sliding block; the motor mounting seat is installed on the other sliding block; and the guide shaft has opposite ends thereof respectively connected with the motor mounting seat and the moving seat.

5. The orthopedic implantation operation system according to claim 4, wherein: there is a pair of said guide shafts, and the pair of guide shafts is provided with two pairs of said sliding blocks thereon, the moving seat is mounted on one pair of sliding blocks, and the motor mounting seat is mounted on the other pair of sliding blocks.

6. The orthopedic implantation operation system according to claim 1, further comprising:
    a guide pin;
    a bottom plate for mounting the linear motor and the linear guide rail thereon; and
    a guide pin fixing mechanism for clamping and fixing the guide pin, comprising:
        a fixing support;
        a connecting rod mounting block;
        a pair of clamping blocks; and
        at least a pair of connecting rods;
    wherein the fixing support is detachably installed on the bottom plate; the connecting rod mounting block is installed on the fixing support, or the fixing support and the connecting rod mounting block are of an integral structure; one end of one of the pair of connecting rods is movably connected to the connecting rod mounting block, and the other end of the one of the pair of connecting rods is connected to one of the pair of clamping blocks; the pair of clamping blocks are locked together by a fastener, so that the guide pin is clamped and fixed between the pair of clamping blocks.

7. The orthopedic implantation operation system according to claim 6, wherein the at least a pair of connecting rods includes a pair of long connecting rods and a pair of short connecting rods; the pair of long connecting rods each has one end rotatably connected with one of opposite sides of the connecting rod mounting block and has the other end connected with the clamping block; the pair of short connecting rods each has one end rotatably connected with one of the opposite sides of the connecting rod mounting seat and has the other end connected and fixed to the clamping block.

8. The orthopedic implantation operation system according to claim 1, further comprising:
    a bottom plate for mounting the linear motor and the linear guide rail thereon;
    a housing mounted on the bottom plate and covering on the linear advancing mechanism and the power drill mechanism;
    a cross-laser system installed at a front end of the housing; and
    a computer electrically connected with the control circuit, or the control circuit set in the computer.

9. The orthopedic implantation operation system according to claim 1, further comprising a surgical robot, wherein the surgical robot controls the linear advancing mechanism and the power drill mechanism through an interface and a sensor.

10. The orthopedic implantation operation system according to claim 1, further comprising:
    a bottom plate for mounting the linear motor and the linear guide rail thereon; and a guide tube mechanism installed at a front end of the bottom plate, comprising:
        a guide tube;
        a guide tube locking seat;
        a guide tube seat;
        an upper and lower adjusting seat; and an adjusting seat;
wherein the guide tube passes through a through hole of the guide tube locking seat; the guide tube locking seat is detachably installed on the guide tube seat; the guide tube seat is installed on the upper and lower adjusting seat, the upper and lower adjusting seat is installed on the adjusting seat, the adjusting seat is installed on the bottom plate; a height and position of the upper and lower adjusting seat is adjustable by means of moving up and down relative to the adjusting seat.

11. The orthopedic implantation operation system according to claim 2, further comprising a clamping mechanism; wherein the clamping mechanism comprises:
a speed reducer; and
a quick -release joint connected with the speed reducer and used for detachably clamping the surgical tool;
an output shaft of the speed reducer is connected with the surgical tool, and the motor of the power drill mechanism is connected with the speed reducer so as to drive the surgical tool rotating through the speed reducer.

12. The orthopedic implantation operation system according to claim 11, wherein the motor of the power drill mechanism is connected with the speed reducer through a torque sensor; one end of a spindle of the torque sensor is coupled to an output shaft of the motor of the power drill mechanism, and the other end thereof is coupled to an input shaft of the speed reducer whereby the motor drives the speed reducer through the torque sensor; and the torque sensor is electrically connected with the control circuit for detecting a torque during the motor drives the spindle of the torque sensor rotating.

13. The orthopedic implantation operation system according to claim 12, wherein the moving seat is provided with a shaft hole; the other end of the spindle of the torque sensor passes through the shaft hole in the moving seat and then is coupled to the input shaft of the speed reducer; a speed reducer mounting seat is provided for supporting the speed reducer; the guide shaft is provided with a bearing; the guide shaft passes through the bearing and has opposite ends thereof respectively connected with the motor mounting seat and the moving seat; the bearing is linearly movable back and forth along the guide shaft; the speed reducer mounting seat is connected to the bearing and linearly movable together with the bearing.

14. The orthopedic implantation operation system according to claim 13, wherein the speed reducer mounting seat is a cover structure installed on the bottom plate; the moving seat and the motor mounting seat are housed in the cover structure; the speed reducer is supported at a front end of the cover structure.

15. The orthopedic implantation operation system according to claim 11, wherein the speed reducer is detachably connected with a speed increaser, the speed increaser is connected with a drill chuck, and the drill chuck is used for clamping the surgical tool; the output shaft of the speed reducer is coupled to an input shaft of the speed increaser to realize speed increase.

16. The orthopedic implantation operation system according to claim 13, further comprising a pressure sensor electrically connected with the control circuit for detecting resistance of the surgical tool during the advancement motion; wherein the pressure sensor is installed on the moving seat, and a sensor fixing block is provided for connecting the pressure sensor with the speed reducer mounting seat so as to detect a pressure according to a relative movement between the speed reducer mounting seat and the moving seat.

17. The orthopedic implantation operation system according to claim 2, wherein a limit switch is provided and electrically connected with the control circuit to limit front and rear positions of the power drill mechanism during the linear reciprocating motion; the limit switch includes a pair of photoelectric switches and a pair of sensing sheets; the pair of photoelectric switches are installed on opposite sides of the bottom plate respectively, and the pair of sensing sheets are installed on the moving seat and the motor mounting seat respectively so as to limit the front and rear positions of the power drill mechanism through a cooperation between the corresponding sensor sheet and the corresponding photoelectric switch.

18. The orthopedic implantation operation system according to claim 11, further comprising a binocular camera; wherein the binocular camera is installed at a front end of the linear advancing mechanism; the power drill mechanism is provided with a navigation surface which forms a visible light visual recognition tracking pattern thereon; and the binocular camera is used for tracking the navigation surface.

19. The orthopedic implantation operation system according to claim 18, wherein the navigation surface is formed on a body of the speed reducer.

* * * * *